United States Patent [19]
Detienne et al.

[11] 4,455,262
[45] Jun. 19, 1984

[54] PROCESS OF PRODUCTION OF ORGANIC DITHIO-ACIDS

[75] Inventors: Jean-Louis Detienne, Pau; Guy Levesque, Ballon; Pierre Tozzolino, Morlaas, all of France

[73] Assignee: Societe Nationale Elf Aquitaine (Production), France

[21] Appl. No.: 368,037

[22] Filed: Apr. 13, 1982

[30] Foreign Application Priority Data

Apr. 15, 1981 [FR] France .............................. 81 07629

[51] Int. Cl.³ .......................................... C07C 153/03
[52] U.S. Cl. ............................. 260/502.6; 260/455 R
[58] Field of Search ............................... 562/426, 512; 260/455 R, 502.6

[56] References Cited

U.S. PATENT DOCUMENTS 1,532,226  4/1925  Codwell ......................... 260/455 R
3,860,641  1/1975  Zengel et al. ........................ 562/512

Primary Examiner—Henry R. Jiles
Assistant Examiner—Robert C. Whittenbaugh
Attorney, Agent, or Firm—Ostrolenk, Faber, Gerb & Soffen

[57] ABSTRACT

Process for the preparation of an organic dithio-acid by reaction of the corresponding dithio-ester and an alkali metal or alkaline earth metal hydrosulphide in a solvent in the presence of an excess of $H_2S$ and treatment with a mineral acid. The dithioic acids so obtained can be utilized as collectors for the flotation of minerals.

11 Claims, No Drawings

PROCESS OF PRODUCTION OF ORGANIC DITHIO-ACIDS

The present invention relates to the preparation of organic dithio-acids; it also relates to the use of these compounds in the flotation of minerals.

Organic dithio-acids are industrial products, the use of which has grown in recent years. They are utilized particularly in cosmetics, most especially in tan-producing anti-sunburn creams and, in a general manner, for compositions which allow protection of the skin against ultraviolet radiation. This application is described in the publication of French Pat. No. 2396545 which also discloses a process in which unsaturated oils are combined with dithioic acids, which gives compounds which protect the skin well against ultraviolet. On the other hand, novel collectors for the flotation of minerals have been prepared following the publication of French Pat. No. 2429617 and according to the Addition No. 7914692 to the latter. These documents describe in particular the use of esters, salts or acids R—S—(CH$_3$)$_n$C-SSOH as collectors in the flotation of minerals such as galena, chalcopyrite, blende, etc.

Thus, the dithioic acids have become industrial products which it is of interest to be able to manufacture economically. However, up till now, the only process which has allowed the direct production of such acids is based upon a reaction of magnesium derivatives, realisation of which is neither simple nor economic. This magnesium route has been described by BERNER and THUILIER in Comptes Rendus de l'Academie des Sciences No 274, page 642 (1972); it has also been the subject of studies by J MEYER, P VERMEER and L BRANDOMA (Recueil de Travaux Chimiques des Pays Bas 1973, No. 92-601), but it has not been made more economical. Thus before this situation the position was that the dithio-acids are difficult to prepare, although there is an easier and more economical method for preparation of the dithio-esters; it is known in fact that the dithio-esters, of the general formula

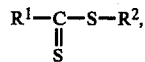

can be obtained by the reaction of a thiol R$^2$—SH with a nitrile R$^1$—C≡N in the presence of anhydrous gaseous HCl, followed by the action of H$_2$S, in accordance with the method of MARVEL and colleagues (Journ. Am.Chem.Soc.77–5997 of 1955).

The present invention is based upon the conception according to which it can be economical to utilize dithio-esters as the starting material for the production of the dithioic acids themselves, if a reaction can be found which allows easy passage of the ester to the acid, without undesirable secondary reactions, such as occurs upon the hydrolysis of thio-esters. Such a reaction has now been found by the Applicants and forms the subject of the present invention.

The novel process according to the invention consists in reacting a sulphur acid of an alkali metal or alkaline earth metal with a dithioic ester, in an anhydrous solvent, and treating the product of the reaction with a mineral acid as concentrated as possible. This reaction can be written as:

As sodium hydrosulphide, NaSH, is most readily accessible industrially, it is mostly employed according to the invention; it is also possible however—and useful in certain cases—to replace it with the corresponding compounds of potassium, calcium, magnesium or others. Moreover, the hydrosulphide can be formed in situ, for example by starting with sodium alcoholate or Na$_2$S, by the action of an excess of H$_2$S, if required under pressure.

Various organic solvents can be utilized, in particular, alcohols or ethers, for example, methanol, ethanol, propanol, ether-glycols, dioxane, etc.

The reaction can take place at ordinary temperature, for example between 0° and 40° C., temperatures of the order of 15° to 25° naturally being most suitable. Depending upon the temperature and the nature of the reactants utilized, the reaction can require several hours or several tens of hours, most frequently from 8 to 24 hours. After this time, a mineral acid is added which causes the sodium salt of the alkali metal hydrosulphide utilised to precipitate; this acid can be hydrochloric, sulphuric, phosphoric, sulphurous or others, hydrochloric acid being highly recommendable both from the standpoint of cost as well as the ease with which it allows precipitation of the alkali metal chloride from the reaction medium. It is convenient to utilize this acid in the form of a very concentrated solution, for example 10N, in order not to dilute the organic solvent with water; injection of gaseous HCl is advantageous from this standpoint.

The precipitated mineral salt, that is to say NaCl most frequently, is separated from the reaction medium and the liquid is subjected to evaporation under reduced pressure; in this way, a product is recovered the major part of which is constituted by the desired dithioic-acid, accompanied by a certain proportion of the non-reacted initial dithio-ester RCS$_2$R'. Separation of the two compounds generally presents no difficulty; it can be effected by fractional distillation, since in general the boiling temperatures of the dithioic acids differ considerably from those of their esters.

As regards the thiol R'SH formed, it can be eliminated during the reaction itself, before or after precipitation of the salt, by degassing, when it is sufficiently volatile; this is the case with methyl mercaptan boiling at 6° C. and also ethyl mercaptan, the boiling point of which is 35° C. These are the most common cases, as in general it is of no interest to utilise dithio-esters in which R' contains more than 2 carbon atoms. However, it is always possible to eliminate the thiol formed by volatilization, at the same time as or before separation of the dithioic acid. It will be noted in passing that recovery of the thiol here is an advantageous operation, because thiols are industrial products of value.

The process of the invention can be applied to a large number of thio-esters, that is to say R can be constituted by organic groups of widely ranging structure and molar size. In a general manner, R is an aliphatic group, more particularly alkyl or alkenyl, where the number of carbon atoms can vary widely, in particular from C$_1$ to C$_{20}$. The aliphatic group can be linear or branched, but—preferably—the side chains should not occupy the alpha position with respect to the acid function; it is preferable for the side chains to be remote from this function, for example in the beta position, which avoids steric hindrance which renders the reaction difficult.

Thus R can be a normal butyl or a 2-methyl-propyl

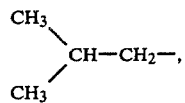

but the reaction becomes very difficult when R is a 1,1-dimethyl-ethyl

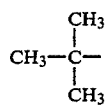

Also, R can be a normal hexyl, a 3-ethyl-butyl,

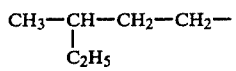

or an aromatic ring. In contrast, the reaction becomes difficult if the ethyl radical substituent is in the 1-position.

On the other hand, the aliphatic groups R can contain other elements and particularly O and/or S, that is, they can be ethers or thio-compounds, for example, ether-glycols or thio-ethers, such as $CH_3$—$CH_2$—$CH_2$—O—$CH_2$—$CH_2$—, $C_{12}H_{25}$—S—$CH_2CH_2$— or the like. The molecule can also contain a second dithioic function, that is the ester utilised can be in the form R'SSC—R"—CSSR'.

As regards the alcohol residue R' of the dithio-esters employed, it can be constituted by various alkyl groups, but—as already mentioned above—both for economic reasons and to facilitate operation, the radical R' is commonly methyl or ethyl. The heavier groups R', particularly $C_6$ to $C_{18}$, can be recommendable, if the dithio-acid to be prepared has a sufficiently low temperature, for example like dithio-acetic acid.

When the group R of the initial dithio-ester has a low molecular weight, as is the case for example with dithio-acetic or dithio-propionic esters, the dithioic acid formed has a relatively low boiling point and its separation from volatile solvents, such as lower alcohols, can be difficult; in this case, the invention provides the utilisation of a heavier solvent, that is to say having a lower vapour pressure than that of the dithioic acid to be separated; such solvents can be selected from polyol ethers, particularly the ethers of diethylene glycol.

The invention also comprises the use of certain dithioic acids and their salts as collectors in the flotation of minerals. As it is already known to employ, as collectors, dithiocarboxylic acids of the type R—S—$(CH_2)_n$CSSH and their soluble salts, as indicated in French Pat. No. 7914692 at the top of page 2, it is not to be expected that acids which do not contain the thio group in the hydrocarbon chain R—S—$(CH_2)_n$— could serve as collectors; according to French Publication No. 2429617 and its Addition No. 7914692, the specific properties of flotation collectors are due to the presence of this thio group, irrespective of the end of the chain of the compound utilized. However, according to the present invention, good collectors can be obtained even without a sulphur atom in the hydrocarbon chain, when this is terminated by a —CSSH or —CSSM group, where M designates an alkali metal or ammonium. However, for the collector to be truly efficacious, it is suitable for its hydrocarbon chain to have a sufficiently high molecular weight, that is it is preferably $C_4$ or above; excellent results are obtained with dithioic acids where the chain is from $C_6$ to $C_{18}$. Thus, for example, good flotation results are obtained with, as collectors, compounds such as dithiolauric, dithiomyristic, dithiopalmitic, dithiooleic etc. acids and their Na, K or NH$_4$ salts.

The non-limitative examples which follow illustrate the preparation of aliphatic dithioic acids by the process of the invention, as well as the use of such acids.

EXAMPLE 1

A solution of 2 moles of sodium methylate in 1 liter of anhydrous methanol is cooled to 3° C.; after this, it is saturated with dry hydrogen sulphide. To the solution so obtained, 2 moles of ethyl dithiopentanoate, $CH_3CH_2CH_2CH_2CSSC_2H_5$, are rapidly added. The solution is maintained at 15° for 15 hours, after which 120 ml of 10N HCl are added to it; sodium chloride precipitates and it is separated by filtration.

The filtrate is evaporated under reduced pressure; the methanol, the excess H$_2$S and HCl as well as the ethyl-mercaptan, $C_2H_5SH$, formed are thus eliminated and a residue is recovered which contains 85% of dithiopentanoic acid, $CH_3CH_2CH_2CH_2CSSH$, the remainder being the unreacted initial dithio-ester. By fractional distillation, these two compounds are separated. It may be noted however that the mixture obtained by this preparation, that is 85 parts of dithiopentanoic acid with 15 parts of ethyl dithiopentanoate, is very suitable as a collector for the flotation of minerals.

EXAMPLE 2

With a view to preparing dithio-acetic acid, the volatility of which is of the same order as that of methanol, the latter is replaced by the monoethyl ether of diethyleneglycol. For this, 2,000 ml of this ether are reacted with 23 g of sodium until total dissolution of the metal; then the solution is saturated with H$_2$S; then 0.95 mole of ethyl dithio-acetate, $CH_3CSSC_2H_5$, is added and the mixture is stirred for 18 hours at 20° C.

The solution is then acidified with 200 ml of a 5N HCl solution in anhydrous ether.

After filtration, the liquid is distilled under reduced pressure, thus eliminating the ether first, for recovery afterwards of the dithio-acetic acid. The yield of this is 65%.

EXAMPLE 3

A solution of 2 moles of anhydrous NaSH per liter of anhydrous methanol is prepared by saturation with H$_2$S of methanol containing 1 mole of anhydrous Na$_2$S. The saturation takes place at +2° C., after which 2 moles of methyl dithiobutyrate, $CH_3CH_2CH_2CSS$—$CH_3$, are added. The mixture is agitated for 16 hours at 17° C. Then, 130 ml of 10N HCl are added and the NaCl precipitated is separated by filtration.

The filtrate is evaporated under vacuum, which allows recovery of the methyl-mercaptan, $CH_3SH$, formed and the methanol. The residue comprises dithiobutyric acid, $CH_3CH_2CH_2CSSH$, in a yield of 87%.

EXAMPLE 4

1 mole of anhydrous $Na_2S$ in 1 liter of the monomethyl ether of ethylene glycol, $CH_3O-CH_2-CH_2-CH_2-OH$, is saturated with excess $H_2S$ at 0° C. Then, 1 mole of methyl dithio-acetate is added and the operation is continued as in Example 2. The dithio-acetic acid is obtained in a yield of 63%.

EXAMPLE 5

A solution of 2 moles of NaSH in the presence of an excess of $H_2S$ in ethyl alcohol, prepared as in Example 3, has 2 moles of ethyl myristyl-thia-1-dithioacetate, $C_{14}H_{29}SCH_2CSSC_2H_5$, added to it. The mixture is agitated for 18 hours, after which 120 ml of 10N HCl are added to it. After separation of the NaCl precipitated and distillation, myristyl-thia-1-dithio-acetic acid, $C_{14}H_{29}SCH_2CSSH$, is recovered in a yield of 71%.

This acid is very useful for the separation of chalcopyrite or galena from their ores.

EXAMPLE 6

A solution of 2 moles of NaSH in methanol, prepared as in Example 3, has 2 moles of ethyl dithio-caproate, $CH_3(CH_2)_4CSSC_2H_5$, added to it. The sequence of operations is the same as in the foregoing examples. Dithio-caproic acid, $CH_3(CH_2)_4CSSH$, is obtained in a yield of 76%.

EXAMPLE 7

Operation is as in the foregoing example, but with ethyl dithio-laurate in place of the dithio-caproate; dithio-lauric acid, $CH_3(CH_2)_{10}CSSH$, is obtained in a yield of 69%.

EXAMPLE 8

2 moles of sodium ethanolate dissolved in 1 liter of anhydrous ethanol are subjected to saturation with $H_2S$ at 5° C. To the solution obtained, 1 mole of ethyl tetra-thioadipate, $C_2H_5-SSC-CH_2CH_2CH_2CH_2-CSSC_2H_5$, is added and the mixture is agitated for 20 hours at 18° C. Then separation of the precipitated NaCl is carried out, followed by fractional distillation, as in the foregoing examples.

Tetrathio-adipic acid, $HSSC-(CH_2)_4-CSSH$, is obtained in a yield of 67%.

EXAMPLES 9 to 14

By the technique described on page 4 of the publication of French Patent No. 2429617, the activity of collectors according to the present invention is assayed on pulps comprising 3.3 g per liter, at pH 5, of various minerals. The following results are obtained.

| Example | Mineral | Collector | % of mineral recovered |
|---|---|---|---|
| 9 | Galena | Dithio-pentanoic acid of Example 1 | 95 |
| 10 | Chalcopyrite | Dithio-pentanoic acid of Example 1 | 94 |
| 11 | Blende | Dithio-pentanoic acid of Example 1 | 46 |
| 12 | Galena | Dithio-lauric acid | 91 |
| 13 | Chalcopyrite | Dithio-lauric acid | 96 |
| 13a | Chalcopyrite | No collector | 32 |
| 14 | Blende | Dithio-lauric acid | 80 |

EXAMPLE 15

A solution of 2 moles of NaSH in methanol, prepared as in Example 3, has added to it 2 moles of carboxymethyl dithio-benzoate, $C_6H_5-CS_2-CH_2-CO_2H$. The mixture is agitated for 16 hours at 17° C. Then 120 ml of 10N HCl are added and the NaCl precipitated is separated by filtration. The filtrate is evaporated under vacuum, which allows recovery of the thioglycolic acid formed and the methanol. The residue comprises dithiobenzoic acid, $C_6H_5-CS_2H$, in a yield of 85%.

EXAMPLE 16

1 g of carboxymethyl-4-vinyl-dithiobenzoate polymer is put into suspension in a solution of 1 g of sodium in 50 ml of anhydrous methanol previously saturated with hydrogen sulphide. (This solution can be replaced by a solution of the equivalent quantity of sodium hydrosulphide in an anhydrous methanol saturated with hydrogen sulphide).

At the end of 1 hour, the polymer is in solution; agitation then continues for 6 hours. Concentrated mineral acid and water are then added; poly(4-vinyl-dithiobenzoic) acid precipitates, which is identified by the usual spectroscopic methods.

Since it is very sensitive to oxidation by air, it must be precipitated with reactants and solvents which are carefully saturated with an inert gas. The polymer has the formula:

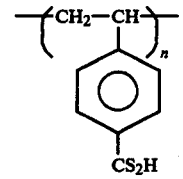

Various copolymers have been obtained from copolymers of carboxymethyl-4-vinyl-dithiobenzoate with styrene, methyl methacrylate, acrylamide, vinylpyrrolidone, methacrylic acid etc. The mode of operation above is modified by the addition of co-solvents which permit solubilization of the copolymer: toluene or dimethylformamide, for example.

We claim:

1. Process for the preparation of a dithioic organic acid from a corresponding ester, characterised in that the dithio-ester is reacted with the hydrosulphide of an alkali metal or alkaline earth metal in an anhydrous organic solvent which is an alcohol, an ether or an ether-alcohol in the presence of excess $H_2S$, and the reaction product is treated with a mineral acid.

2. Process according to claim 1, characterised in that the alkali metal or alkaline earth metal salt formed with the added mineral acid is separated from the reaction medium and the remaining liquid is subjected to fractional distillation.

3. Process according to claim 1 or 2, characterised in that the alkali metal hydrosulphide is that of sodium hydrosulphide.

4. Process according to claim 3, characterised in that the reaction takes place at a temperature from 0° to 40° C., before addition of the mineral acid, in particular very concentrated hydrochloric acid.

5. Process according to claim 3, characterised in that in the dithio-ester employed is RCSSR′, the group R is aliphatic, linear or branched, the side-chains if present being located in positions remote from the alpha position with respect to the —CSS-function.

6. Process according to claim 5, characterised in that the aliphatic chain R includes at least one oxygen or sulphur atom.

7. Process according to claim 1, characterised in that the dithio-ester carries a second dithioic function.

8. Process according to claim 1 or 2, characterized in that the alkali metal hydrosulphide is formed in situ by the reaction of $H_2S$ with the corresponding sulphide or alcoholate.

9. Process according to claim 1, characterized in that the solvent is methyl alcohol, ethyl alcohol or a glycol ether.

10. Process according to claim 4, characterized in that the reaction takes place at a temperature between 15° and 25° C. for 8 to 24 hours and the mineral acid is concentrated hydrochloric acid.

11. Process according to claim 5 in which the group R is $C_1$ to $C_{20}$ alkyl or alkenyl, linear or branched, and the side chains, if present, are in the beta-position with respect to the —CSS-function.

* * * * *